(12) United States Patent
Anderson

(10) Patent No.: US 11,260,520 B2
(45) Date of Patent: Mar. 1, 2022

(54) PUMICE DEVICE AND HANDLE

(71) Applicant: UNITED STATES PUMICE COMPANY, Chatsworth, CA (US)

(72) Inventor: Elizabeth Anderson, Chatsworth, CA (US)

(73) Assignee: United States Pumice Company, Chatsworth, CA (US)

( * ) Notice: Subject to any disclaimer, the term of this patent is extended or adjusted under 35 U.S.C. 154(b) by 623 days.

(21) Appl. No.: 15/462,461

(22) Filed: Mar. 17, 2017

(65) Prior Publication Data
US 2018/0264639 A1 Sep. 20, 2018

(51) Int. Cl.
| | | |
|---|---|---|
| *B25G 1/10* | (2006.01) | |
| *A61B 17/54* | (2006.01) | |
| *A47L 13/42* | (2006.01) | |
| *B25G 3/14* | (2006.01) | |
| *A61B 17/00* | (2006.01) | |

(Continued)

(52) U.S. Cl.
CPC .............. *B25G 1/102* (2013.01); *A47L 13/42* (2013.01); *A61B 17/54* (2013.01); *B25G 3/14* (2013.01); *A61B 2017/00424* (2013.01); *A61B 2017/320004* (2013.01); *B29C 65/4815* (2013.01); *B29C 66/301* (2013.01); *B29L 2031/74* (2013.01)

(58) Field of Classification Search
CPC ........ A47K 7/028; A47K 7/026; A47K 7/022; A47K 7/02; A45D 29/04; A45D 29/00; A45D 2200/1054; A61B 17/54; Y10T 16/498; Y10T 16/469; B24D 15/084; B25G 1/00; B25G 1/10; B25G 1/102; B25G 3/12; B25G 3/18; B25G 1/105; B25B 23/0007; B25B 23/0021
USPC ...... 132/75.6, 76.4, 76.5; D28/59; 15/176.1, 15/176.2, 176.6, 143.1–145, 84; 451/524, 451/557; 81/489
See application file for complete search history.

(56) References Cited

U.S. PATENT DOCUMENTS 1,617,015 A * 2/1927 De Vivo ................ B24D 15/08
51/309
2,334,690 A * 11/1943 Yden ........................ B08B 9/38
15/211

(Continued)

FOREIGN PATENT DOCUMENTS

JP 3080691 U * 10/2001
JP 3085006 U 4/2002

OTHER PUBLICATIONS

US Pumice, Pumie Toilet Bowl Ring Removal, Mar. 5, 2016 (Year: 2016).*

(Continued)

*Primary Examiner* — Tatiana L Nobrega
*Assistant Examiner* — Sarah Woodhouse
(74) *Attorney, Agent, or Firm* — Lewis Roca Rothgerber Christie LLP (57) ABSTRACT

A handle configured to be attached to a pumice stone. The handle includes a gripping portion and a post extending from the gripping portion. The post is configured to support the pumice stone. The post includes a support member, a series of ribs spaced apart along a length of the support member, and a series of cavities defined between adjacent ribs. The cavities are configured to accommodate an adhesive for coupling the post of the handle to the pumice stone.

13 Claims, 4 Drawing Sheets

(51) Int. Cl.
  *B29C 65/48* (2006.01)
  *B29C 65/00* (2006.01)
  *A61B 17/32* (2006.01)
  *B29L 31/00* (2006.01)

(56) References Cited

U.S. PATENT DOCUMENTS

| | | | | |
|---|---|---|---|---|
| 2,610,354 A * | 9/1952 | Howell | ................... | B25G 3/00 16/422 |
| 2,810,150 A * | 10/1957 | Ellman | ................... | B25G 3/00 15/244.1 |
| 2,908,930 A * | 10/1959 | Gasper | ................... | A47L 13/46 15/210.1 |
| 3,231,921 A * | 2/1966 | Cuervo | ................... | A47L 17/00 15/244.1 |
| 4,461,053 A * | 7/1984 | Nitzsche | ................... | A46B 7/04 15/145 |
| 4,811,445 A * | 3/1989 | Lagieski | ............... | A46B 5/0095 15/104.94 |
| 4,856,136 A * | 8/1989 | Janssen | ................... | A46B 3/02 15/244.3 |
| 4,886,388 A * | 12/1989 | Gulker | ................... | A47K 7/028 401/148 |
| 4,887,994 A * | 12/1989 | Bedford | ............... | A61M 35/006 604/1 |
| 4,909,650 A * | 3/1990 | Gilbert | ................... | A45D 40/26 15/104.94 |
| 5,003,660 A * | 4/1991 | Oohinata | ............... | A45D 40/28 15/244.1 |
| 5,366,314 A | 11/1994 | Young | | |
| 5,513,665 A * | 5/1996 | Chan | ................... | A45D 4/10 132/227 |
| 5,630,244 A * | 5/1997 | Chang | ................... | A46B 5/0062 15/143.1 |
| 5,758,381 A * | 6/1998 | Rocha | ................... | A47K 7/026 15/104.92 |
| 5,855,214 A * | 1/1999 | Heneghan | ............... | A45D 40/28 132/317 |
| 5,908,644 A * | 6/1999 | Poole | ................... | E04F 21/1652 425/458 |
| 6,557,212 B2 | 5/2003 | Huang | ................... | B25G 3/26 15/145 |
| 6,902,056 B2 * | 6/2005 | Dotterman | ............ | A47K 11/10 206/361 |
| 7,181,800 B2 | 2/2007 | Lee | | |
| 7,771,135 B2 | 8/2010 | Bizzotto | | |
| 8,926,205 B1 * | 1/2015 | Allen | ................... | A47K 5/05 401/88 |
| 9,775,486 B2 * | 10/2017 | Dotterman | ............ | A47L 13/44 |
| 2002/0148058 A1 | 10/2002 | Greenwood et al. | | |
| 2003/0172946 A1 * | 9/2003 | Choe | ................... | A45D 29/05 132/76.4 |
| 2005/0019086 A1 * | 1/2005 | Haneda | ................... | A45D 34/00 401/123 |
| 2005/0055789 A1 * | 3/2005 | Kubes | ................... | A47K 11/10 15/210.1 |
| 2005/0138748 A1 * | 6/2005 | Cisneros | ............... | A47K 11/10 15/210.1 |
| 2006/0033229 A1 * | 2/2006 | Daley | ................... | B29C 41/22 264/109 |
| 2006/0070197 A1 * | 4/2006 | May | ................... | B25G 1/04 15/144.1 |
| 2006/0185108 A1 * | 8/2006 | Hoadley | ............... | A47L 13/16 15/209.1 |
| 2008/0250588 A1 * | 10/2008 | Robinson | ............... | A47K 11/10 15/104.05 |
| 2012/0117743 A1 * | 5/2012 | Yang | ................... | A47L 13/38 15/231 |
| 2014/0137352 A1 * | 5/2014 | Golla | ................... | A47K 7/028 15/160 |
| 2017/0203430 A1 * | 7/2017 | Tomm | ................... | A46B 9/02 |
| 2018/0290287 A1 * | 10/2018 | Rohlfs | ................... | B25G 3/14 |

OTHER PUBLICATIONS

Webstaurant, Pumie-Jan-6-Toilet-Bowl-Ring-Remover, 2015 (Year: 2015).*
Sierra Club, Where Can I Recycle #3 Through #6 Plastic, Sep. 21, 2015 (Year: 2015).*
Revlon, Exfoliator, Dec. 23, 2013 (Year: 2013).*
Written Opinion of the International Preliminary Examining Authority for Application No. PCT/US2018/023014, dated May 14, 2019, 5 pages.
International Search Report and Written Opinion for Application No. PCT/US2018/023014, dated Jul. 9, 2018, 14 pages.
International Preliminary Report on Patentability for International Application No. PCT/US2018/023014, dated Jul. 15, 2019, 7 pages.
Chinese Office action for Patent Application No. 201880012934.3, dated Mar. 9, 2020, 15 pages.

* cited by examiner

PUMICE DEVICE AND HANDLE

FIELD

The present disclosure relates generally to handles.

BACKGROUND

Pumice stones have a variety of uses, including as an exfoliator for removing rough, dry skin from a user's body (e.g., a user's heels) and as a cleaning product (e.g., a scouring product for removing mineral deposits, rust, and/or stains on household appliances). Pumice stones used in the cleaning of appliances with potential hazardous waste such as a toilet or urinal, are typically provided with a handle to protect the user from direct contact with the appliance containing said waste. However, conventional handles may be prone to detaching from the pumice stone, which makes it difficult or impracticable to use the pumice stone. Additionally, conventional handles for pumice stones consume a lot of material and these materials may not be recyclable. Accordingly, many conventional handles for pumice stones are not environmentally friendly. Furthermore, many conventional handles for pumice stones are not ergonomically shaped to be comfortably grasped by a user, which may result in discomfort and/or fatigue in the user's hand while using the pumice stone.

SUMMARY

The present disclosure is directed to various embodiments of a handle configured to support a pumice stone or other object. In one embodiment, the handle includes a gripping portion and a support portion extending from the gripping portion. The support portion is configured to support the pumice stone or other object. The support portion includes a post, a series of ribs spaced apart along a length of the post, and a series of cavities defined between adjacent ribs. The series of cavities is configured to accommodate an adhesive for coupling the support portion of the handle to the pumice stone. The handle may include a base member between the gripping portion and the support portion. The support portion extends from a first surface of the base member and the gripping portion extends from a second surface of the base member opposite to the first surface. Adjacent ribs may be spaced apart by a distance from approximately ⅛ inch to approximately ½ inch. The support portion may include a first vertical strut bisecting a second vertical strut to form a post having a cross shape. Each rib may include a series of rib segments arranged in a common plane. Each rib segment may be a quadrant. Each of the rib segments may extend between the first and second braces. The handle may be made of polypropylene, such as a pure polypropylene suitable for level 5 recycling.

In another embodiment, the handle includes a support portion configured to support the pumice stone and a gripping portion extending from the support portion. The gripping portion includes a first arm comprising a first surface and a second surface opposite the first surface, a second arm spaced apart from the first arm, the second arm comprising a first surface and a second surface opposite the first surface, a substantially planar platform extending between the first arm and the second arm and spaced apart from each of the first and second surfaces, and an interconnecting portion extending between distal ends of the first and second arms. The first and second arms and the platform may define a first opening proximate to the support portion and a second opening proximate to the interconnecting portion. An upper surface of the each of the first and second arms may be curved away from a lower surface of a corresponding arm of the first and second arms. The first surface of each of the first and second arms defines a recess extending longitudinally along a central portion thereof, toward the substantially planar platform such that a transverse distance between the planar platform and each of the first surfaces is less than a transverse distance between the planar platform and each of the second surfaces, the recess comprising a lower straight segment having a length greater than a length of the planar platform. The platform may include at least one indicium, such as a recycling symbol, a trademark, and/or an identification of a material of the handle. The handle may also include base member between the gripping portion and the support portion. The support portion extends from a first surface of the base member and the gripping portion extends from a second surface of the base member opposite to the first surface.

The present disclosure is also directed to various embodiments of a pumice stone device. In one embodiment, the pumice stone device includes a pumice stone defining a central opening at a first side thereof and a handle extending along a longitudinal direction and attached to the pumice stone. The handle includes a gripping portion and a support portion extending from the gripping portion. The gripping portion of the handle includes a first arm extending longitudinally and comprising a first surface and second surface opposite the first surface, a second arm extending longitudinally and spaced apart from the first arm, the second arm comprising a first surface and a second surface opposite the first surface, a substantially planar platform extending between the first arm and the second arm and spaced apart from each of the first and second surfaces, and an interconnecting portion extending between distal ends of the first and second arms. The support portion of the handle extends into the opening in the pumice stone. The support portion includes a post, a series of ribs spaced apart along a length of the post, and a series of cavities defined between adjacent ribs. The pumice stone device also includes an adhesive in the plurality of cavities securing the handle to the pumice stone. The adhesive may be a hot melt glue. The handle further may include a base member between the gripping portion and the support portion supporting an end of the pumice stone. The first and second arms and the platform may define a first opening proximate to the base member and a second opening distal to the base member. The platform may include at least one indicium, such as a recycling symbol, a trademark, and/or an identification of a material of the handle.

This summary is provided to introduce a selection of concepts that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

The present disclosure is directed to various embodiments of a handle. The handles of the present disclosure may be used, for instance, to support a pumice stone. In one or more embodiments, the handles of the present disclosure are configured to accommodate an adhesive (e.g., a hot melt glue) for attaching the handle to the pumice stone or other object. Additionally, in one or more embodiments, the handles of the present disclosure have an ergonomic shape to enable a user to comfortably grasp the handle and use the handles for prolonged periods of time with minimal or at least reduced fatigue compared to conventional handles. The handles according to various embodiments of the present disclosure are configured to reduce an amount of material used to manufacture the handle compared to conventional handles and the material used to manufacture the handle may be recyclable. Additionally, the handle according to various embodiments of the present disclosure includes one or more enlarged openings for mounting or supporting the handle on hooks commonly used in retail displays. The handles according to various embodiments of the present disclosure may also include a planar surface including various indicia, such as a trademark, a recycling symbol, and/or an identification of the material of the handle.

Figure 1A:
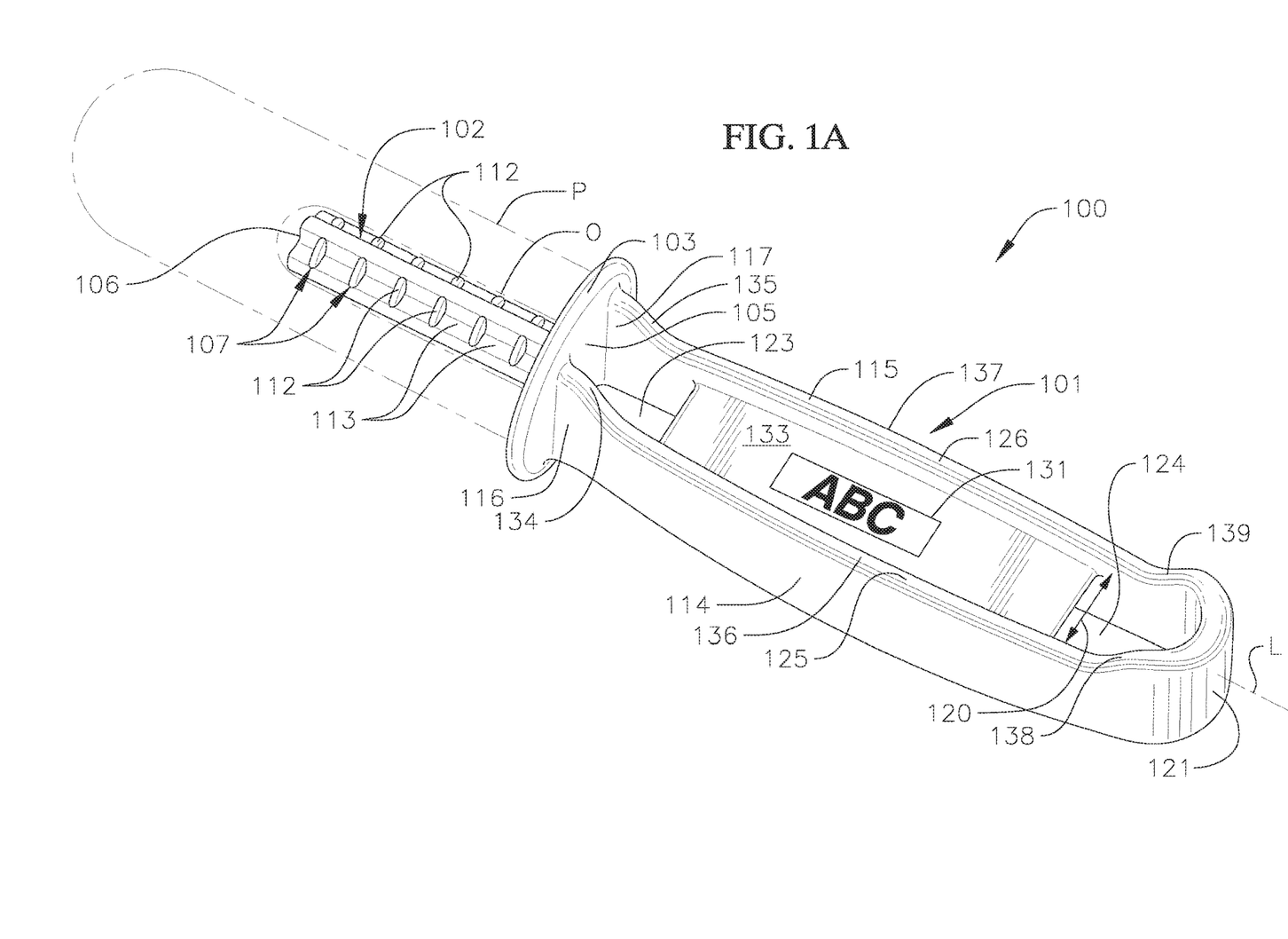
FIGS. 1A-1B are perspective views of a handle according to one embodiment of the present disclosure attached to a pumice stone.
Figure 1B:
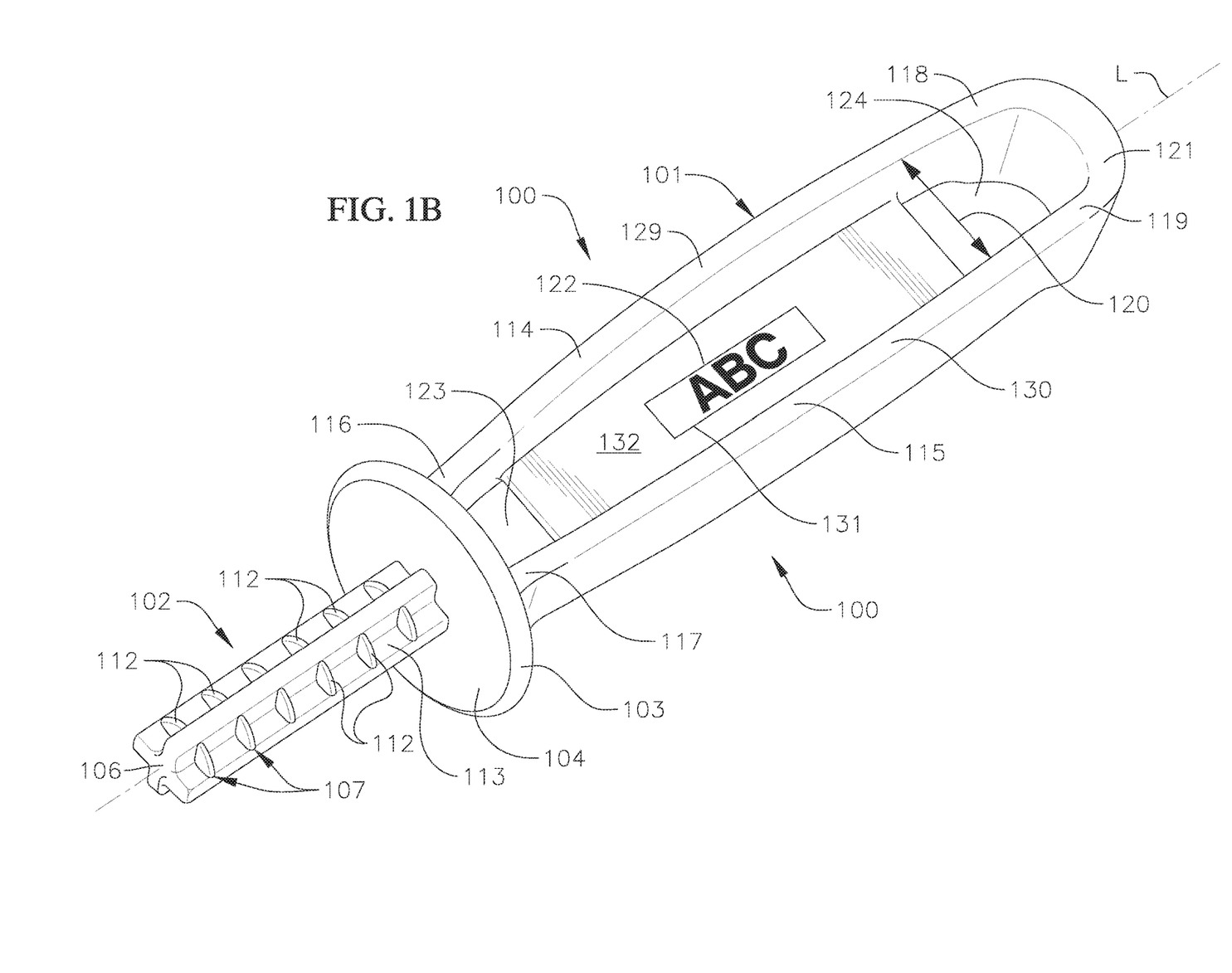
Figure 2:
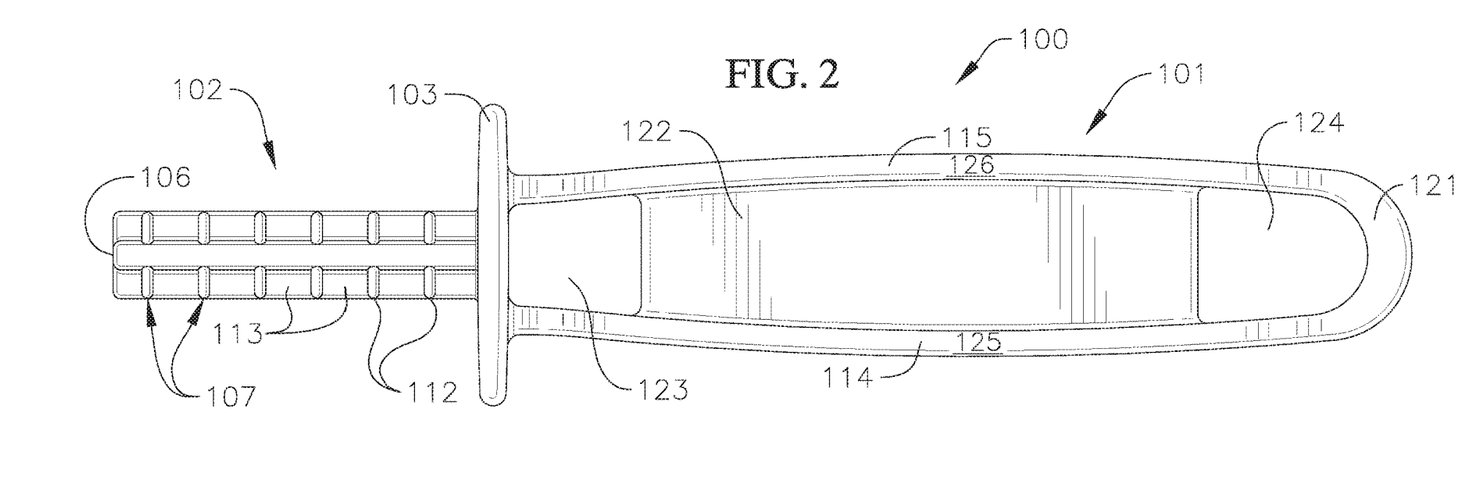
FIG. 2 is a bottom view of the embodiment of the handle depicted in FIG. 1.
Figure 3:
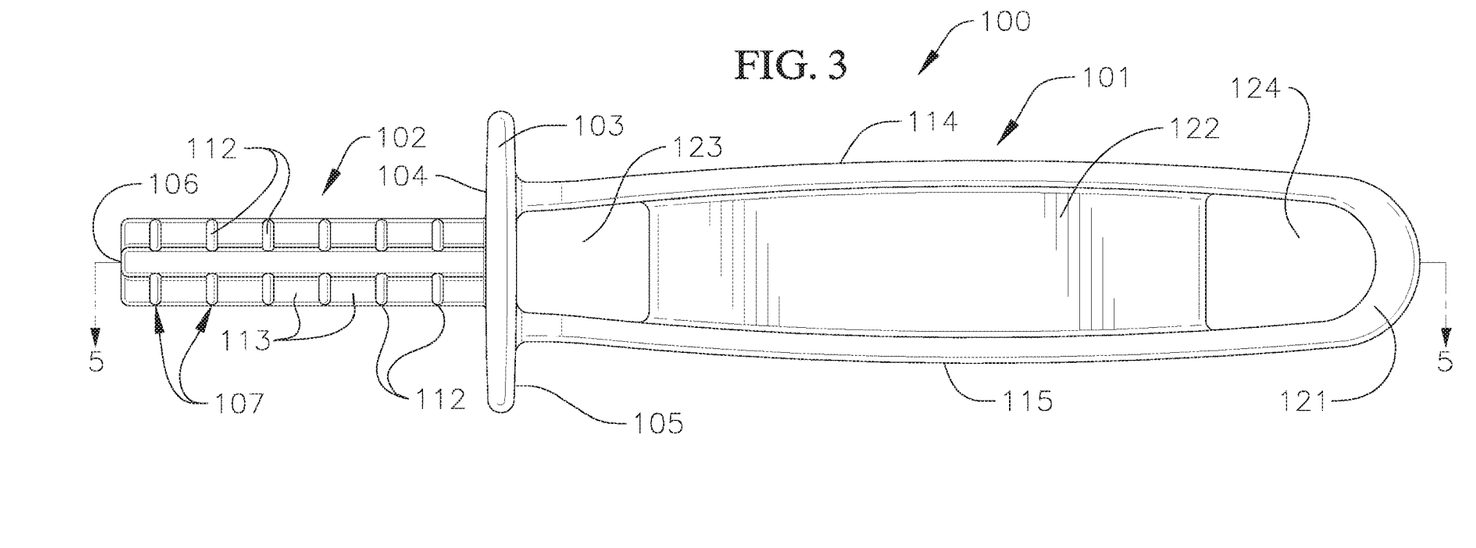
FIG. 3 is a top view of the embodiment of the handle depicted in FIG. 1.
Figure 4:
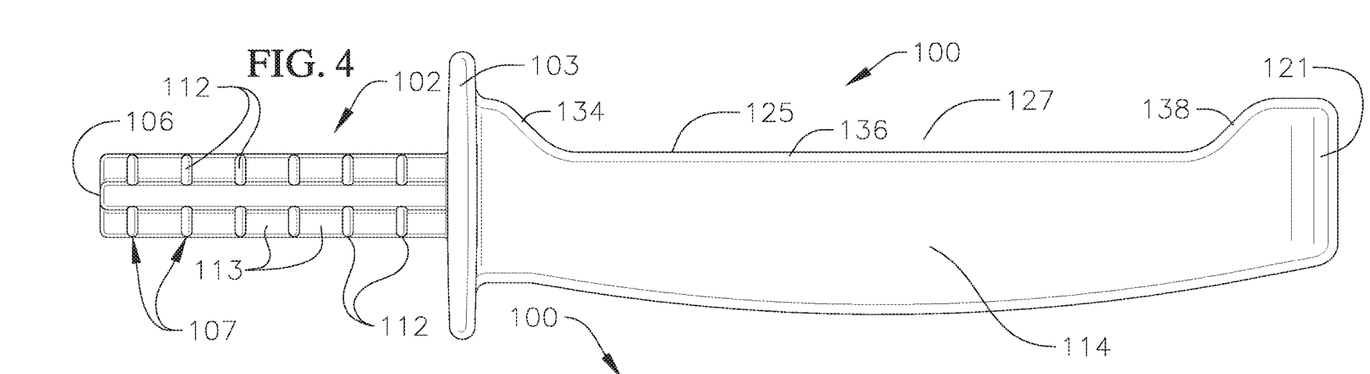
FIG. 4 is a side view of the embodiment of the handle depicted in FIG. 1.
Figures 5, 6:
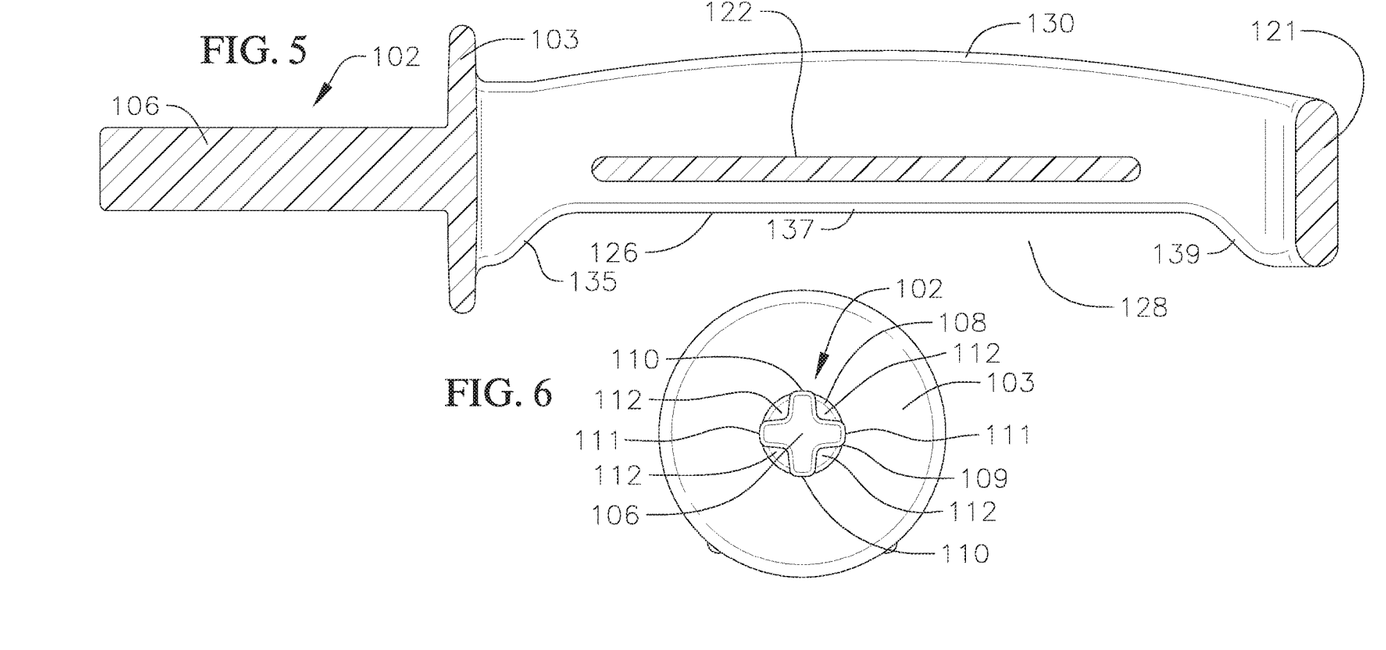
FIG. 5 is a cross-sectional view of the embodiment of the handle depicted in FIG. 1 taken along line A-A in FIG. 3.
FIG. 6 is an end view of the embodiment of the handle depicted in FIG. 1.

With reference now to FIGS. 1A-6, a handle 100 according to one embodiment of the present disclosure includes a gripping portion 101 configured to be grasped by a user, and a support portion 102 extending from the gripping portion 101. In the illustrated embodiment, the support portion 102 is shown supporting a pumice stone P by extending into an opening O (e.g., a blind central axial opening or a through hole) in the pumice stone P, although in one or more embodiments the support portion 102 may be used to support any other object. The support portion 102 may have any length suitable for the size of the pumice stone P or other object the handle 100 is configured to support. In one or more embodiments, the support portion 102 may have a length from approximately 1 inch to approximately 2 inches (e.g., approximately 1.6 inches). The gripping portion 101 may have any suitable length, such as, for instance, from approximately 3 inches to approximately 5 inches (e.g., approximately 4 inches).

Additionally, in the illustrated embodiment, the handle 100 includes a base member 103 between the gripping portion 101 and the support portion 102. In the illustrated embodiment, the support portion 102 extends from an inner surface 104 of the base member 103 and the gripping portion 102 extends from an outer surface 105 of the base member 103 opposite to the inner surface 104. In the illustrated embodiment, the base member 103 is disc-shaped and has an outer diameter from approximately 0.5 inch to approximately 2 inches. In one or more embodiments, the base member 103 may have any other suitable size and any other suitable shape, such as, for instance, a prismatic shape (e.g., a square prismatic shape). In the illustrated embodiment, the base member 103 is configured to support an end of the pumice stone P.

With continued reference to the embodiment illustrated in FIGS. 1A-6, the support portion 102 includes a post 106 and a series of ribs 107 spaced apart along a length of the post 106. In the illustrated embodiment, the post 106 has a cross shape including a first strut 108 (e.g., a vertical strut) and a second strut 109 (e.g., a horizontal strut) bisecting the first strut 108. Although in the illustrated embodiment the second strut 109 bisects the first strut 108 at a right angle or substantially a right angle, in one or more embodiments, the first and second struts 108, 109 may bisect each other at any other suitable angles. Additionally, as illustrated most clearly in FIG. 6, ends 110, 111 of the first and second struts 108, 109, respectively, are drafted such that the ends 110, 111 of the first and second struts 108, 109 taper radially inward (e.g., the first and second struts 108, 109 each taper between relatively wider outer ends and relatively narrower inner ends). In one or more embodiments, the first and second struts 108, 109 may be drafted at any suitable angle, such as, for instance, a draft angle from approximately 1 degree to approximately 3 degrees (e.g., approximately 2 degrees). Additionally, in one or more embodiments, the post 106 may have any other suitable configuration, such as, for instance, any other suitable prismatic shape (e.g., a square prismatic shape) or a non-prismatic shape (e.g., cylindrical). Additionally, although in the illustrated embodiment the support portion 102 is uniform or substantially uniform, in one or more embodiments, the support portion 102 may taper (e.g., the support portion 102 may taper from a larger end proximate to the base member 103 to a smaller end distal to the base member 103).

With continued reference to FIGS. 1A-6, each rib 107 includes a series of angular rib segments 112 (i.e., in the illustrated embodiment, each rib 107 is defined by a series of planar or substantially planar rib segments 112). Additionally, in the illustrated embodiment, each of the rib segments 112 extends between the first strut 108 and the second strut 109. In the illustrated embodiment, each rib segment 112 is a quadrant or substantially a quadrant (i.e., a quarter of a disc). Together, the rib segments 112 in the illustrated embodiment define generally round (e.g., circular) ribs 107. In one or more embodiments, the rib segments 112 may have any other suitable shapes, such as, for instance, triangular, square, or rectangular, such that the ribs 107 may have any suitable shape, such as, for instance, a prismatic shape. Accordingly, although in the illustrated embodiment each of the ribs 107 includes a curved outer edge (e.g., an arcuate outer edge), in one or more embodiments the outer edges of the ribs 107 may be straight or substantially straight or may have any other suitable shape. Moreover, although in the illustrated embodiment the support portion 102 includes six ribs 107 equidistantly spaced along the post 106, in one or more embodiments, the support portion 102 may include any other suitable number of ribs 107 and the ribs 107 may be irregularly spaced along the post 106. Additionally, although in the illustrated embodiment each rib 107 is defined by four rib segments 112, in one or more embodiments, each rib 107 may be defined by any other suitable number of rib segments 112 (e.g., fewer than four rib segments 112 or more than four rib segments 112).

Furthermore, in one or more embodiments, each rib 107 may be a single, continuous member.

With continued reference to the embodiment illustrated in FIGS. 1A-6, a series of cavities 113 (e.g., recesses) are defined between adjacent rib segments 112. In the illustrated embodiment, each cavity 113 is defined between an adjacent pair of rib segments 112 and portions of the first and second struts 108, 109 extending between the adjacent pair of rib segments 112. In one or more embodiments, adjacent rib segments 112 of adjacent ribs 107 may be spaced apart from each other by approximately ⅛ inch to approximately ½ inch, such as, for instance, approximately ¼ inch. Accordingly, in one or more embodiments, the cavities 113 may each have a length along the post 106 from approximately ⅛ inch to approximately ½ inch, such as, for instance, approximately ¼ inch. The cavities 113, which are each defined between adjacent pairs of rib segments 112 and the portions of the first and second struts 108, 109 extending between the adjacent pairs of rib segments 112, are configured to accommodate an amount of an adhesive (e.g., a hot melt glue) for securing the handle 100 to the pumice stone P (see FIG. 1A) or other object. The rib segments 112, which define the inner and outer ends of the cavities 113 along the support portion 102, are configured to evenly or substantially distribute the adhesive along the post 106 by preventing or mitigating the adhesive from collecting at one end of the support portion 102 or collecting only at certain portions along the support portion 102. Evenly distributing the adhesive along the support portion 102 is configured to form a uniform or substantially uniform attachment between the support portion 102 of the handle 100 and the pumice stone P or other object. Without the ribs 107, the adhesive might tend to collect at (e.g., flow to) an end of the support portion 102 (e.g., the adhesive might tend to flow to and collect at the end of the support portion 102 proximate to the base member 103). Collection of the adhesive at an end of the support portion 102 could cause only that portion of the support portion 102 to be adhered or sufficiently adhered to the pumice stone P, which may result in an insufficiently robust connection between the support portion 102 of the handle 100 and the pumice stone P that could lead to premature failure and inadvertent detachment of the handle 100 from the pumice stone P.

In one or more embodiments, the support portion 102 may have any other configuration suitable for attaching the handle 100 to the pumice stone P. For instance, in one or more embodiments, the support portion 102 may be provided without the ribs 107 (e.g., the support portion 102 may be provided with only the post 106 and the post 106 may have any suitable shape, such as a cylindrical rod, a tapered cylindrical rod, a prismatic shape, such as a square prismatic shape, or a tapered prismatic shape, such as a frusto-pyramidal shape). In one or more embodiments, the support portion 102 of the handle 100 may be provided without the ribs 107 and the cavities 113 may be defined directly in the post 106 (e.g., the cavities 113 configured to receive the adhesive may be defined by recesses directly in the post 106 rather than by the ribs 107).

In the illustrated embodiment, the gripping portion 101 of the handle 100 includes a pair of arms 114, 115 each having a proximal end 116, 117 at the base member 103 and a distal end 118, 119 opposite to the proximal end 116, 117, respectively. In the illustrated embodiment, the arms 114, 115 are spaced apart from each other by a gap 120. In one or more embodiments, the gap 120 may be from approximately 0.5 inch to approximately 1 inch. Additionally, in the illustrated embodiment, the arms 114, 115 are curved outward with respect to a centerline L of the gripping portion 101, although in one or more embodiments, the arms 114, 115 may be parallel or substantially parallel to the centerline L of the gripping portion 101 or may curve inward with respect to the centerline L. Curving the arms 114, 115 outward with respect to the centerline L of the gripping portion 101 is configured to provide an ergonomic configuration for a user to grasp the gripping portion 101.

Additionally, in the illustrated embodiment, the gripping portion 101 includes an interconnection portion 121 extending between and interconnecting the distal ends 118, 119 of the arms 114, 115. In the illustrated embodiment, the interconnection portion 121 is rounded (e.g., having a radius from approximately ¼ inch to approximately ½ inch, such as, for instance, approximately ⅜ inch), although in one or more embodiments, the interconnection portion 121 may have any other suitable shape, such as straight.

In the illustrated embodiment, the gripping portion 101 also includes a platform 122 extending between the arms 114, 115. In the illustrated embodiment, the platform 122 is a generally planar rectangular member, although in one or more embodiments, the platform 122 may have any other suitable shape. The platform 122 is configured to increase the structural rigidity of the gripping portion 101 by, for example, preventing the arms 114, 115 from moving closer toward each other when a user grasps the gripping portion 101. Additionally, various indicia 131 may be provided on one or more surfaces of the platform 122, including trademark indicia, a recycling symbol configured to promote recycling the handle, and/or an identification of the material of the handle 100. The indicia 131 may be provided on an upper surface 132 and/or a lower surface 133 of the platform 122.

Additionally, in the illustrated embodiment, the platform 122 does not extend completely to the proximal ends 116, 117 of the arms 114, 115 at the base member 103 and does not extend completely to the interconnection portion 121 at the distal ends 118, 119 of the arms 114, 115. Accordingly, in the illustrated embodiment, a pair of openings 123, 124 are defined at opposite ends of the gripping portion 101 (i.e., a proximal opening 123 is defined between a proximal end of the platform 122 and the base member 103 and a distal opening 124 is defined between the distal end of the platform 122 and the interconnection portion 121). The openings 123, 124 are configured to permit the handle 100 to be displayed in a retail store, such as, for instance, hung on a hook in a retail store display. Although in the illustrated embodiment the gripping portion 101 defines two openings 123, 124, in one or more embodiments, the gripping portion 101 may define a single opening (e.g., the distal opening or the proximal opening).

With continued reference to the embodiment illustrated in FIGS. 1A-6, lower surfaces 125, 126 of the arms 114, 115 define a pair of recesses 127, 128 (see FIGS. 4 and 5), respectively, configured to accommodate a user's fingers when the user grasps the gripping portion 101 of the handle 100. In the illustrated embodiment, the lower surface 125, 126 of each arm 114, 115 slopes upward from a proximal end 134, 135 of the arm 114, 115 at the base member 103, extends straight along an intermediate section 136, 137 of the arm 114, 115, and slopes downward at a distal end 138, 139 of the arm 114, 115 proximate to the interconnection portion 121. The proximal and distal ends 134, 135 and 138, 139, respectively, of the lower surfaces 125, 126 of the arms 114, 115 may taper at any suitable angle, such as, for instance, from approximately 30 degrees to approximately 60 degrees (e.g., approximately 45 degrees). Additionally, in the illustrated embodiment, upper surfaces 129, 130 of the arms 114, 115 opposite to the lower surfaces 125, 126 are curved in a direction away from the lower surfaces 125, 126 of the arms 114, 115. Together, the recesses 127, 128 defined in the lower surfaces 125, 126 of the arms 114, 115 and the curved upper surfaces 129, 130 of the arms 114, 115 provide an ergonomic configuration for the user to grasp the gripping portion 101 of the handle 100.

The handle 100 may be made out of any suitable material or materials, such as polypropylene. In one or more embodiments, the handle 100 may be made out of pure or substantially pure polypropylene such that the handle 100 is suitable for level 5 recycling category. Additionally, in one or more embodiments, the use of pure or substantially pure polypropylene permits the handle 100 to be recyclable without sacrificing the tensile strength of the handle 100. Furthermore, the configuration of the handle 100 according to one or more embodiments of the present disclosure uses less material (e.g., approximately 50% less polypropylene) than conventional handles such that the handle 100 is more environmentally friendly than conventional handles.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims. Although relative terms such as "outer," "inner," "upper," "lower," "below," "above," and similar terms have been used herein to describe a spatial relationship of one element to another, it is understood that these terms are intended to encompass different orientations of the various elements and components of the invention in addition to the orientation depicted in the figures. Additionally, as used herein, the term "substantially" and similar terms are used as terms of approximation and not as terms of degree, and are intended to account for the inherent deviations in measured or calculated values that would be recognized by those of ordinary skill in the art. Furthermore, as used herein, when a component is referred to as being "on" another component, it can be directly on the other component or components may also be present therebetween. Moreover, when a component is component is referred to as being "coupled" to another component, it can be directly attached to the other component or intervening components may be present therebetween.

What is claimed is:

1. A pumice device comprising:
   a pumice comprising a central opening at a first side thereof; and
   a handle extending along a longitudinal direction and comprising:
      a gripping portion comprising:
         a first arm extending longitudinally and comprising a first surface and second surface opposite the first surface;
         a second arm extending longitudinally and spaced apart from the first arm, the second arm comprising a first surface and a second surface opposite the first surface; and
         a substantially planar platform extending between the first arm and the second arm, and spaced apart from each of the first and second surfaces,
   wherein the first surface of each of the first and second arms defines a recess extending longitudinally along a central portion thereof, toward the substantially planar portion such that a transverse distance between the planar platform and each of the first surfaces is less than a transverse distance between the planar platform and each of the second surfaces, the recess comprising a lower straight segment having a length greater than a length of the planar platform, a first tapered segment at a distal end of the lower straight segment, and a second tapered segment at a proximal end of the lower straight segment, and
   wherein the second surface of each of the first and second arms is curved outward away from the recess and the substantially planar portion; and
   a support portion extending from the gripping portion and extending into the opening of the pumice, the support portion comprising:
      a first vertical strut bisecting a second horizontal strut to form a post having a cross shape,
      a plurality of ribs each extending circumferentially around an axial centerline of the post and arranged spaced apart along a length of the post, each rib of the plurality of ribs comprising four rib segments disposed between adjacent portions of the vertical and horizontal struts, and
      a plurality of cavities defined between adjacent ribs of the plurality of ribs, and
      an adhesive disposed in the plurality of cavities, the adhesive securing the handle to the pumice stone along the central opening thereof.

2. The pumice device of claim 1, wherein the handle further comprises a base member between the gripping portion and the support portion, the support portion extending from a first surface of the base member, the gripping portion extending from a second surface of the base member opposite to the first surface.

3. The pumice device of claim 1, wherein the adjacent ribs of the plurality of ribs are spaced apart by a distance from approximately ⅛ inch to approximately ½ inch.

4. The pumice device of claim 3, wherein the four rib segments of each rib are arranged in a common plane.

5. The pumice device of claim 4, wherein each rib segment of the plurality of rib segments is a quadrant.

6. The pumice device of claim 1, wherein the handle comprises polypropylene.

7. The pumice device of claim 6, wherein the polypropylene is a pure polypropylene suitable for level 5 recycling.

8. A pumice device comprising:
   a pumice comprising a central opening at a first side thereof;
   a handle a extending along a longitudinal direction and comprising:
      a gripping portion comprising:
         a first arm extending longitudinally and comprising a first surface and a second surface opposite the first surface:
         a second arm extending longitudinally and spaced apart from the first arm, the second arm comprising a first surface and a second surface opposite the first surface; and
         a substantially planar platform extending between the first arm and the second arm, and spaced apart from each of the first and second surfaces; and
      an interconnecting portion extending between distal ends of the first and second arms, wherein the first surface of each of the first and second arms defines a recess extending longitudinally along a central portion thereof, toward the substantially planar portion such that a transverse distance between the planar platform and each of the first surfaces is less than a transverse distance between the planar platform and each of the second surfaces, the recess comprising a lower straight segment having a length greater than a length of the planar platform, a first tapered segment at a distal end of the lower straight segment, and a second tapered segment at a proximal end of the lower straight segment, and wherein the second surface of each of the first and second arms is curved outward away from the recess and the substantially planar portion; and a support portion extending from the gripping portion and extending into the opening of the pumice, the support portion comprising:
- a first vertical strut bisecting a second horizontal strut to form a post having a cross shape,
- a plurality of ribs each extending circumferentially around an axial centerline of the post and arranged spaced apart along a length of the post, each rib of the plurality of ribs comprising four rib segments disposed between adjacent portions of the vertical and horizontal struts, and
- a plurality of cavities defined between adjacent ribs of the plurality of ribs, and an adhesive disposed in the plurality of cavities, the adhesive securing the handle to the pumice stone along a central opening thereof.

9. The pumice device of claim 8, wherein the adhesive is a hot melt glue.

10. The pumice device of claim 8, wherein the handle further comprises a base member between the gripping portion and the support portion, the base member supporting the first side of the pumice.

11. The pumice device of claim 10, wherein the first and second arms and the platform define a first opening proximate to the base member and a second opening distal to the base member.

12. The pumice device of claim 8, wherein the platform further comprises at least one indicium selected from the group of indicia consisting of a recycling symbol, a trademark, and an identification of a material of the handle.

13. The pumice device of claim 8, wherein the adhesive is evenly distributed within the plurality of cavities.

* * * * *